United States Patent [19]

Reinertson et al.

[11] 4,213,348
[45] Jul. 22, 1980

[54] SELF-CALIBRATING AUTOMATIC ZEROING STRAIN GAUGE CIRCUIT

[75] Inventors: John E. Reinertson, Cedar Rapids, Iowa; John L. Wells, Los Altos, Calif.

[73] Assignee: MedaSonics, Inc., Mountain View, Calif.

[21] Appl. No.: 62,718

[22] Filed: Aug. 1, 1979

[51] Int. Cl.³ .................. G01L 9/04; G01L 27/00
[52] U.S. Cl. ...................... 73/765; 73/769; 73/726; 324/130
[58] Field of Search ............. 73/763, 765, 766, 769, 73/726, 727, 725; 324/130; 128/672

[56] References Cited

U.S. PATENT DOCUMENTS

| 3,894,535 | 7/1975 | Cannon et al. ............ 128/672 |
| 4,041,382 | 8/1977 | Washburn ................. 324/130 |

*Primary Examiner*—James J. Gill
*Attorney, Agent, or Firm*—Warren M. Becker

[57] ABSTRACT

A method of and apparatus for calibrating and providing an output from a strain gauge (1) is described. In the method and apparatus there is provided a constant-current source (10). Coupled to the current source (10) is an amplifier (12,13) for providing an output corresponding to the difference between the voltage drop across the strain gauge (1) and a reference voltage from a source (14). The reference voltage is used to adjust the current in the strain gauge (1) from the current source (10). After the current is adjusted, further changes in the voltage drop in the strain gauge (1) relative to the reference voltage is used for providing an output of the voltage difference relative to the reference voltage. The adjusting of the magnitude of the current from the constant-current source (10) is provided by a calibrate-and-zero sample and hold circuit (16) having a sample and hold period sufficient to reduce to negligible levels the effects of the dielectric absorption of an associated capacitive means (20).

13 Claims, 6 Drawing Figures

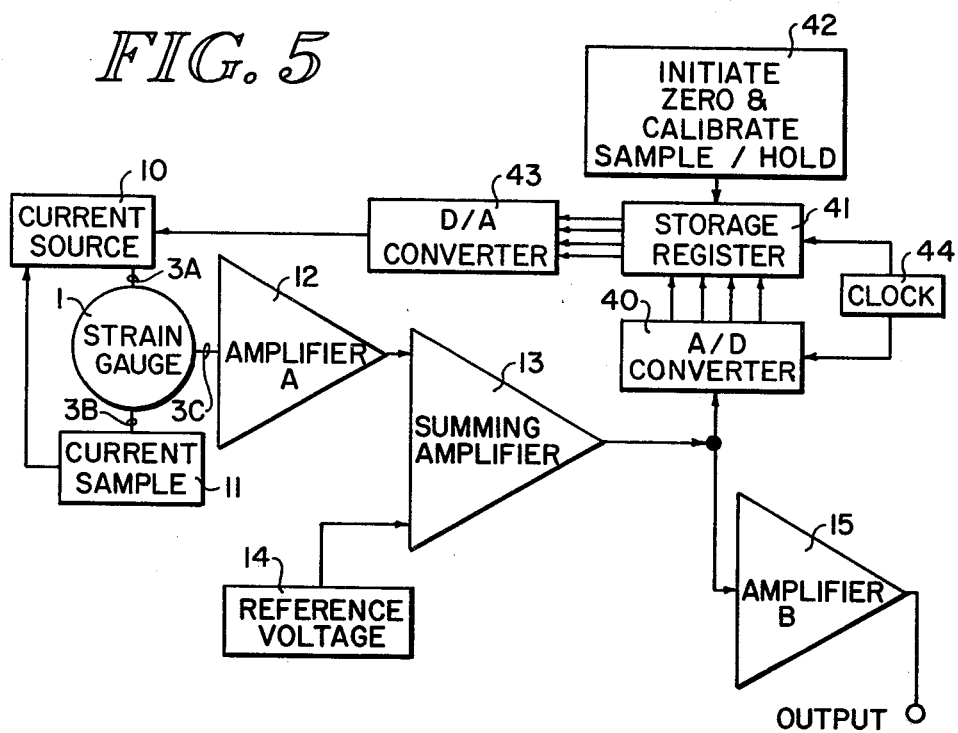
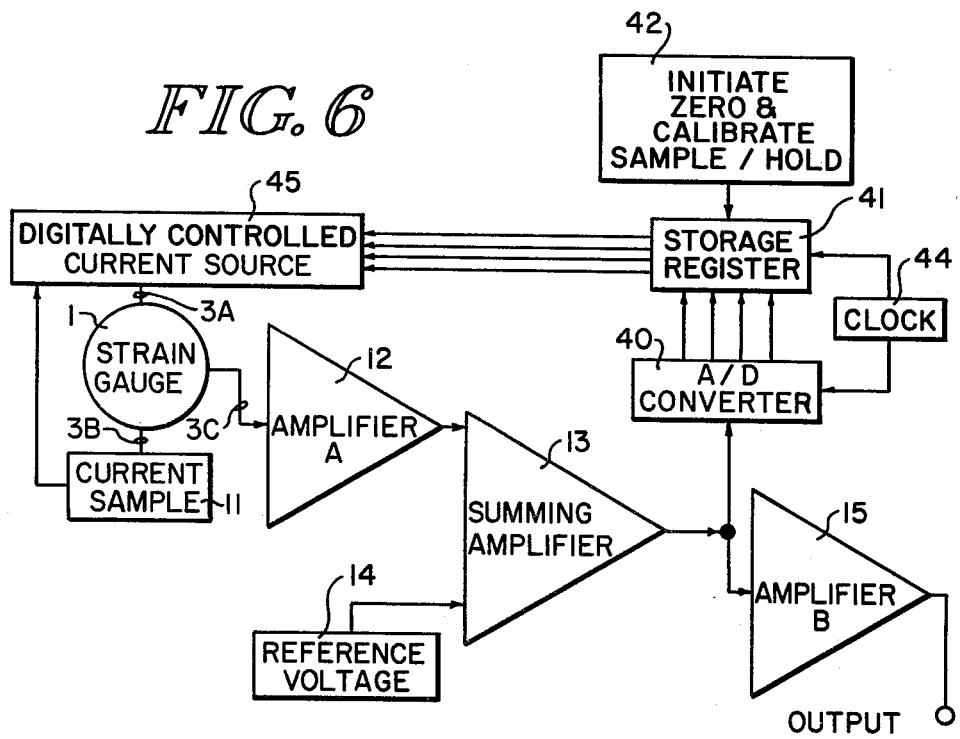

SELF-CALIBRATING AUTOMATIC ZEROING STRAIN GAUGE CIRCUIT

BACKGROUND OF THE INVENTION

The present invention relates to strain gauge circuits in general, and in particular to a self-calibrating strain gauge circuit with automatic zeroing.

Strain gauges are widely used for the dynamic testing and measuring of objects of all kinds in a variety of applications, including medical applications. One such use of a strain gauge in a medical application is in plethysmography. For example, a plethysmography, a strain gauge is used for measuring and recording changes in the volume of a region of an individual's appendage (finger, arm, leg, foot, etc.) caused by a change in the amount of blood inside the region. As blood flows into the region, the girth of the region increases and as blood flows from the region the girth of the region decreases. This includes the short- term changes caused by the pulse and longer venous changes, often in conjunction with a period of intentional venous constriction. As the changes occur, they are recorded. The magnitude and speed of the changes thus recorded can be used to assess the condition of the circulatory system in the region of the appendage being examined and to diagnose problems that may exist therein.

In the plethysmograph system the strain gauge serves as a transducer. It provides a resistance change which is proportional to any change in the size of the girth of the appendage on which it is fitted. Since, for any given appendage, its length is constant, a change in its volume is proportional to a change in its girth.

To record changes in girth, the strain gauge, in the form of a thin silicon rubber tube filled with an electrically conductive material, is wrapped about the appendage. As blood flows through the appendage, changing the size of the appendage, the girth of the appendage changes. A change in the size of the girth of the appendage stretches or relaxes the tube, depending on whether the blood flows in or from the appendage. The stretching and relaxation of the tube changes the resistance of the material contained in the tube. By measuring the resistance change in the tube, an output proportional to the flow of blood in the appendage is obtained.

In a relaxed condition a strain gauge has a predetermined resistance. When the gauge is placed on an appendage, such as an arm or leg, it is stretched. The amount of the stretching of the gauge may differ each time it is used, but nevertheless the stretching results in a change in the gauge resistance. The magnitude of the change in the gauge resistance depends on the size of the appendage and the amount of the stretching when the gauge is fitted. A change in resistance also occurs when the gauge is repeatedly placed on a particular appendage as well as when it is moved from one appendage to another. Because of these initial gauge resistance changes when a gauge is fitted, in order for an operator using a particular gauge to compare readings obtained during successive uses of the gauge or to compare readings obtained from different gauges, it is necessary to calibrate gauges each time they are used.

Another feature of known conventional strain gauge circuits involves variations in the initial or nominal size of a strain gauge when it is fitted to objects of widely differing sizes. This affects the scale required of an output indicator. In the absence of suitable calibration of the output indicator, the gauge input may readily exceed the range of the indicator. For example, as a given gauge is fitted to appendages of successively larger girth, the initial or nominal resistance of the gauge is higher each time. If the scale of the indicator is insufficient to handle possible excursions relative to each nominal resistance, accurate readings are not possible. It, therefore, is highly desirable to have a circuit which normalizes the output of a gauge independently of its resistance.

Heretofore the calibration of strain gauges in general, and those used in strain gauge plethysmography in particular, have been tedious and time-consuming. Conventional calibration was not done on an object to be examined but typically involved the use of models. And, in general, it has required burdensome record keeping to record the necessary figures.

SUMMARY OF THE INVENTION

In view of the foregoing, a principal object of the present invention is a strain gauge circuit for automatically calibrating and providing an output from a strain guage after the strain gauge is fitted to an object to be examined.

Another object of the present invention is a circuit for calibrating and providing an output for a strain gauge after the strain gauge is fitted to an object to be examined which automatically converts strain gauge resistance changes into voltages in a manner which eliminates the need for separate calibration of the system, provides automatically the conditions for accurate size change determination and sets a zero base line independent of the length and resistance of the strain gauge being used.

Another object of the present invention is a circuit for calibrating and providing an output from a strain gauge after the strain gauge is fitted to an object to be examined which may be used for obtaining recordings which can be compared directly with recordings from another and quite different strain gauge.

In accordance with the above objects there is provided in a circuit according to the present invention a constant current source. During calibrating of the strain gauge system, current from the source in the strain gauge is adjusted to provide a voltage drop across the strain gauge which corresponds to a reference voltage. Thereafter, all voltage changes across the strain gauge represent a percentage change in the magnitude of the voltage drop relative to the reference voltage.

A principal feature of the circuit described is a sample and hold circuit. The sample and hold circuit comprises a capacitor which is charged for a predetermined period of time. The time period is sufficient to reduce to negligible levels the effects of the dielectric absorption of the capacitor. The charge accumulated by the capacitor during the predetermined time period is thereafter used for adjusting the magnitude of the current from the constant current source in the strain gauge.

In an alternative embodiment, the "sample and hold" function is implemented digitally. In this embodiment there is provided an A/D converter, a digital storage register without the long-term voltage decay characteristic of a holding capacitor, and a D/A converter to present an analog feedback voltage to the current source. This embodiment is preferred in many systems, when the added complexity is justified by the improved "holding" performance.

In still another embodiment, small temperature-drift errors in the analog-controlled current source are removed by replacing the D/A converter and the analog-controlled current source with a direct digitally-controlled current source coupled to the output of the storage register.

BRIEF DESCRIPTION OF THE DRAWING

The above and other objects, features and advantages of the present invention will become apparent from the following detailed description of the accompanying drawing in which:

FIG. 5 is a block diagram of an alternative embodiment according to the present invention with digital circuits for controlling the output of a constant current source.

FIG. 6 is a block diagram of still another embodiment of the present invention with a digitally-controlled current source.

DETAILED DESCRIPTION

Figure 1:
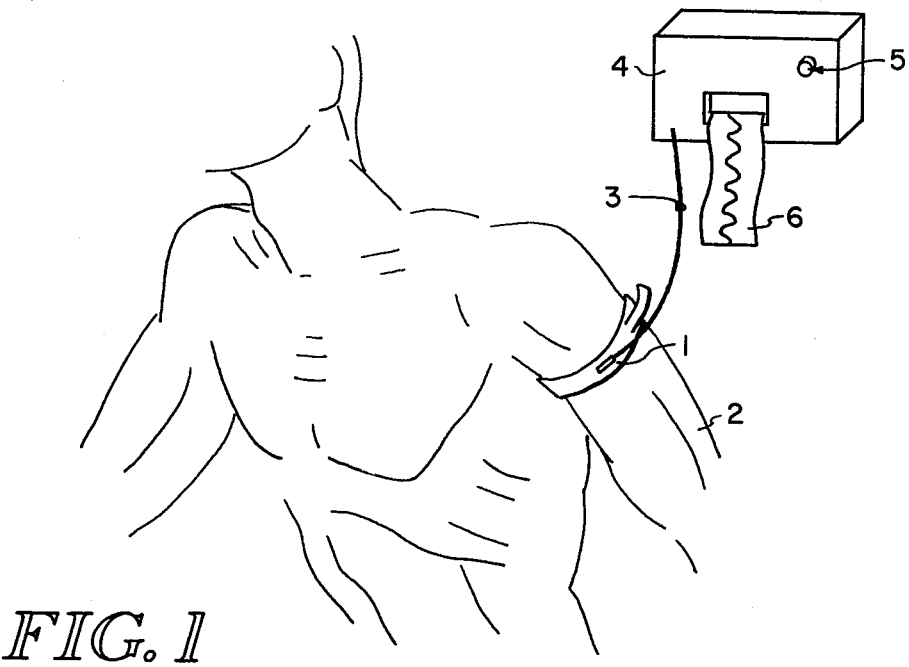
FIG. 1 is a schematic representation of a strain gauge plethysmograph system according to the present invention.

Referring to FIG. 1, there is represented a person having a strain gauge 1 fitted to an arm 2. Coupled to the strain gauge 1 by means of an electrical cable 3, there is provided in accordance with the present invention a self-calibrating strain gauge circuit apparatus with automatic zeroing 4. In the apparatus 4 there is provided a start pushbutton switch 5 and a chart recorder for providing a chart 6 of the blood flow in the arm 2.

Figure 2:
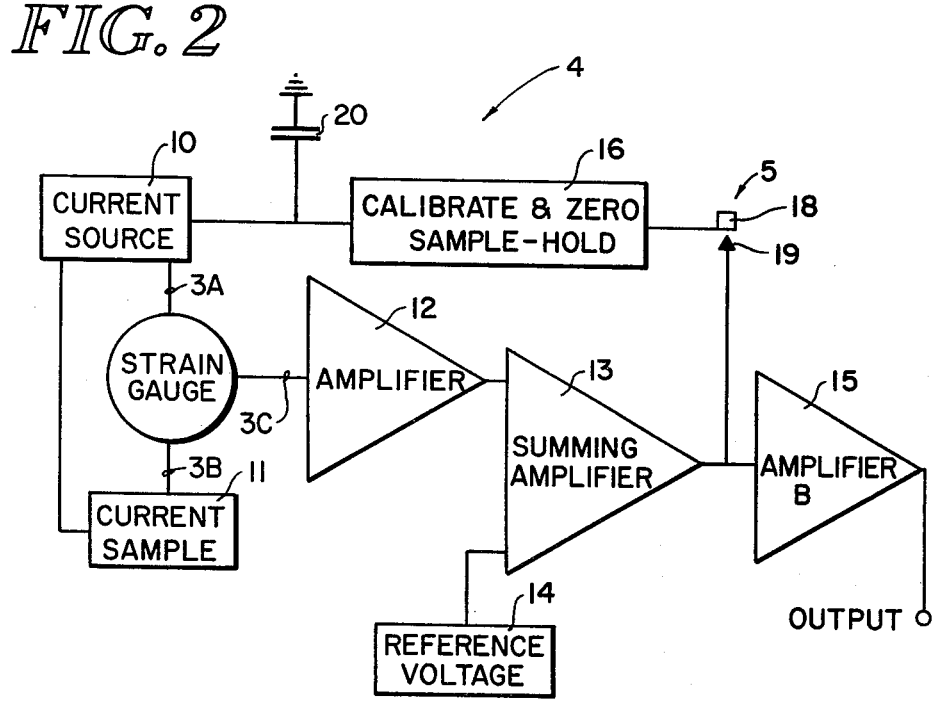
FIG. 2 is a block diagram of a circuit for calibrating and providing an output from a strain gauge according to the present invention.

Referring to FIG. 2, there is shown a block diagram of the circuit of the apparatus 4. In the circuit there is provided a constant-current source 10 and a current-sampling circuit 11. The constant-current source 10 is coupled to the strain gauge 1 as by a wire 3A and the current-sampling circuit 11 is coupled to the strain gauge 1 as by a wire 3B. The wires 3A and 3B form a part of the cable 3. The current-sampling circuit 11 is in turn coupled to the current source 10 for stabilizing the current from the current source 10 by means of negative feedback.

Also coupled to the strain gauge 1 by means of a wire 3C in the cable 3, there is provided an amplifier 12. The output of amplifier 12 is coupled to one input of a summing amplifier 13. Another input of the summing amplifier 13 is coupled to a source of reference voltage 14. Coupled to the output of the summing amplifier 13 there is provided an amplifier 15 and a calibrate-and-zero sample and hold circuit 16. The calibrate-and-zero sample and hold circuit 16 is coupled to the output of the summing amplifier 13 by means of the pushbutton 5 having a movable member 18 and a contact 19. Forming an integral part of the calibrate-and-zero sample and hold circuit 16, but shown separately, there is provided a capacitive means such as a capacitor 20, the function of which is to be described. Typically, the dielectric of the capacitor is polycarbonate of polystyrene. However, cost and size are constraints on the type of capacitor which may be used as a practical matter in a particular application.

Figure 3:
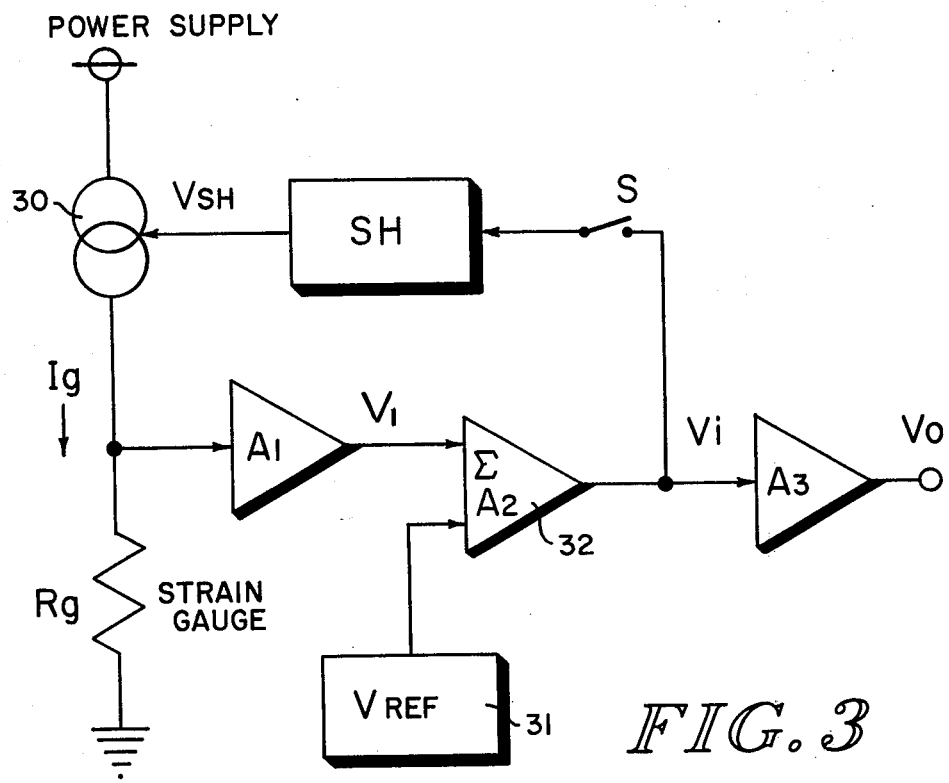
FIG. 3 is a simplified circuit diagram for describing the theory of operation of a circuit according to the present invention.

Referring to FIG. 3, there is shown a block diagram of a circuit which is useful in explaining the theory of operation of the self-calibrating and automatic zeroing strain gauge circuit of the present invention. As seen in FIG. 3, there is provided a constant-current source 30 which outputs a constant current $I_g$. The output of the current source 30 is coupled to a strain gauge $R_g$. Coupled across the strain gauge $R_g$ there is provided an amplifier $A_1$. The magnitude of the current $I_g$ from the source 30 is determined by the output of a sample-hold amplifier SH. The output of a voltage reference source 31 and the output of the amplifier $A_1$ are coupled to the input of a summing amplifier $A_2$. The output of the summing amplifier $A_2$ is coupled to an amplifier $A_3$, and, through a switch S, to the input of the sample-hold amplifier SH. The output, $V_o$, of the amplifier $A_3$ provides an indication of blood flow in the appendage to which the strain gauge is fitted, as will be explained.

In operation, when the switch S is closed, the sample-hold amplifier SH is placed in a sample mode. The sample-hold amplifier SH, when in the sample mode, produces an output voltage, $V_{SH}$. The voltage $V_{SH}$ is inversely proportional to its input voltage $V_i$ providing a negative feedback voltage which controls the strain gauge current $I_g$. The strain gauge current $I_g$ affects $V_1$ and thus $V_i$ as previously explained. Because $V_{SH}$ is an inverse function of $V_i$, the circuit will balance itself through the negative feedback loop such that $V_i$ will be reduced to zero.

When $V_i$ is reduced to zero, the switch S is opened. Thereafter, the hold function of the sample-hold amplifier SH will hold $I_g$ at a fixed value (regardless of changes in $R_g$) until the sample-hold cycle is reactivated by closing switch S. In practice, the sample-hold amplifier SH comprises an insulated gate FET-input operational amplifier with a capacitor at its input.

To begin with, it is assumed that $I_g$ is variable and set by the value of $R_g$. The gains of amplifiers $A_2$ and $A_3$ are fixed, with $A_3$ being larger than $A_2$. In this circuit the output voltage, $V_o$ has the following relationship:

$$V_o = A_3 V_i = A_2 A_3 (V_1 - V_{REF}) \qquad (1)$$

If $R_g$ is fixed (not varying), $$V_1 = A_1 I_g R_g \qquad (2)$$

and $$V_o = A_2 A_3 (A_1 I_g R_g - V_{REF}) \qquad (3)$$

The condition for balance is $$V_o = V_i = 0 \qquad (4)$$

which occurs when $V_1 = V_{REF}$.
Setting equation (3) equal to zero, $$A_2 A_3 (A_1 I_g R_g - V_{REF}) = 0 \qquad (5)$$

$$A_1 I_g R_g - V_{REF} = 0 \qquad (6)$$

$$I_g = V_{REF} / A_1 R_g \qquad (7)$$

Now if the strain gauge is stretched slightly, its resistance becomes $R_g + \Delta R_g$; and equation (3) becomes $$V_o = A_2 A_3 [A_1 I_g (R_g + \Delta R_g) - V_{REF}] \quad (8)$$

Substituting equation (7) in equation (8), $$V_o = A_2 A_3 \left[ A_1 \frac{V_{REF}}{A_1 R_g} (R_g + \Delta R_g) - V_{REF} \right] \quad (9)$$

$$V_o = A_2 A_3 V_{REF} \frac{\Delta R_g}{R_g} \quad (10)$$

Since $A_2$, $A_3$, and $V_{REF}$ are constants, $$V_o = K \Delta R_g / R_g \quad (11)$$

Thus the output voltage is a constant times the fractional change in gauge resistance and independent of gauge current and the gain of $A_1$.

Figure 4:
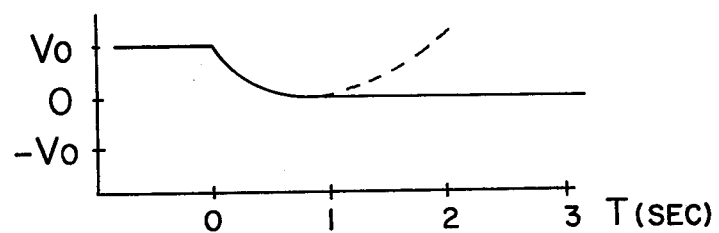
FIG. 4 is a graphical representation of the d.c. component of an output of a circuit according to the present invention.

Referring to FIG. 4, there is shown a diagram of the DC component of the voltage $V_o$ on the output of the amplifier 15 before, at the time of, and after the activation of switch 5. Before the activation of switch 5, which is designated in FIG. 4 as T=0, the voltage $V_o$ at the output of the amplifier 15 is at a relatively high level, determined by the voltage drop across the strain gauge 1 after the strain gauge is fitted to an appendage such as the arm 2 of the person shown in FIG. 1. The voltage $V_o$ is at a high level if, as is typical, the output of the amplifier 12, corresponding to the voltage drop across the strain gauge 1 is higher than the reference voltage from the reference voltage source 14. When the switch or pushbutton 5 is depressed, coupling the output of the amplifier 13 to the input of the calibrate-and-zero sample and hold circuit 16, the capacitor 20 begins to charge. The charging of the capacitor 20 continues until the current from the current source 10 in the strain gauge 1 has been reduced such that the voltage drop across the strain gauge 1 produces an output from the amplifier 12 which equals the reference voltage from the reference voltage source 14. When the output from the amplifier 12 equals the voltage from the reference voltage source 14, the output of the amplifier 13 is substantially reduced to 0.

Even after the output of the summing amplifier 13 is substantially reduced to 0, the output of the summing amplifier 13 remains connected to the calibrate-and-zero sample and hold circuit 16 for a period of at least 2 seconds. The period of 2 seconds is chosen as a period of time sufficient to reduce to negligible levels the effects of the dielectric absorption in the capacitor 20. If, as represented in FIG. 4 by the dashed line, the sampling period was less than 2 seconds, the voltage on the capacitor due to its characteristic dielectric absorption would drift or creep toward a potential corresponding to its previous charge—namely, $V_o$. On the other hand, by setting a sample period of 2 seconds, the potential across the capacitor 20 does not drift at a rate sufficient to degrade the performance of the apparatus.

After the time period has elapsed, any change in the voltage drop across the strain gauge circuit 1 will appear on the output of the amplifier 15 as a fractional change relative to the reference voltage or, in terms of gauge resistance, as a fractional change in gauge resistance.

Referring to FIG. 5, there is provided in an alternative embodiment of the present invention digital circuits for controlling the output of the current source 10 without the long-term voltage decay characteristic of a holding capacitor such as the capacitor 20 of the embodiment of FIG. 2. In the circuit of FIG. 5, there is coupled to the output of the summing amplifier 13 and A/D converter 40, a storage register 41, an initiate zero-and-calibrate sample and hold circuit 42, a D/A converter 43 and a clock circuit 44. The A/D converter 40 is provided for converting the analog output of the summing amplifier 13 to a digital signal for storage in the storage register 41. The D/A converter 43 is provided for converting the digital output from the storage register 41 to an analog signal for controlling the output of the constant current source 10. The clock 44 is provided for synchronizing the A/D converter 40 and the storage register 41. Initiate circuit 42 is in the nature of a control circuit for controlling the conversion and storage of the output of the summing amplifier 13 in the storage register 41 during the calibrate of sample mode of the apparatus.

During the calibrate mode of the apparatus, the summing amplifier 13 has an output corresponding to the difference between the output of the strain gauge 1 and the output of the reference voltage source 14. This output is converted by the A/D converter 40 and stored as a digital number conveniently called the calibrate number in the storage register 41. As the calibrate number is stored in the storage register 41, it is converted by the D/A converter 43 for controlling the output of the current source 10. In practice, the sampling of the output of the summing amplifier 13 and the readjustment of the output of the current source 10 during the calibrate mode continues until the output of the summing amplifier 13 is reduced to zero in a conventional manner.

When the output of the summing amplifier 13 is reduced to zero, the apparatus of FIG. 5 enters the operation or hold mode in which an output from the summing amplifier 13 represents a fractional change relative to the reference voltage or, in terms of gauge resistance, as a fractional change in gauge resistance. As described above with reference to the apparatus of FIGS. 1 and 2, the output of amplifier 15 is recorded for recording these fractional changes.

Referring to FIG. 6, there is provided in still another embodiment of the present invention, a digitally-controlled current source 45 in place of the analog-controlled current source 10. The replacing of the analog current source 10 by the digitally-controlled current source 45 is for removing small temperature-drift errors from the apparatus which are characteristic of analog-controlled sources. In replacing the current source 10 by the digitally-controlled current source 45, the D/A converter 43 is omitted and the output of the storage register 41 is directly coupled to the control circuits of the digitally-controlled current source 45. In all other respects, the apparatus of FIG. 6 is identical to the apparatus of FIG. 5 and performs in the same manner as that described with respect to the apparatus of FIG. 5.

While several embodiments of the current invention are described, it is contemplated that still other changes and modifications to the embodiments described may be made without departing from the spirit and scope of the present invention. Accordingly, it is intended that the scope of the present invention not be limited to the embodiments described but be determined by reference to the claims hereinafter provided and their equivalents.

What is claimed is:

1. A circuit for calibrating and providing an output from a strain gauge after said strain gauge is fitted to an object to be measured comprising:

a constant current source for providing a constant current in said strain gauge;

a source of a reference voltage; means responsive to an error signal corresponding to a difference between a voltage drop across said strain gauge due to said constant current and said reference voltage during a predetermined time period for adjusting the magnitude of the current from said current source in said strain gauge to reduce said difference between said strain gauge voltage drop and said reference voltage; and means responsive to a difference between said voltage drop across said strain gauge and said reference voltage after said adjusting of said current in said strain gauge for providing an output of said voltage difference relative to said reference voltage.

2. A circuit according to claim 1 wherein said means for adjusting said current from said current source in said strain gauge comprises capacitive means responsive to a signal corresponding to the difference between said voltage drop and said reference voltage during said predetermined time period for providing said error signal.

3. A circuit according to claim 1 wherein said current-adjusting means comprises:

a summing amplifying means having a first input coupled to said strain gauge and a second input coupled to said reference voltage source;

a sample and hold circuit coupled to the output of said summing amplifying means; and means for coupling said sample and hold circuit to said constant current source.

4. A circuit according to claim 1 wherein said means for adjusting said current from said current source in said strain gauge comprises:

means for providing a digital calibrating signal corresponding to the magnitude of said error signal;

means for storing said digital calibrating signal; and means responsive to an output from said storing means for adjusting the magnitude of the current from said current source by an amount corresponding to the magnitude of said stored digital calibrating signal.

5. A circuit according to claim 2 wherein said predetermined time period is sufficient to reduce to negligible levels the effects of the dielectric absorption of said capacitive means.

6. A circuit according to claim 4 wherein said current source is a digitally-controlled current source and comprising means for coupling said digitally-controlled current source to the output of said storing means.

7. A circuit according to claim 3 wherein said sample and hold circuit comprises a capacitor circuit means and means for coupling said capacitive circuit means to the output of said summing amplifying means for said predetermined time period.

8. A circuit according to claim 7 wherein said coupling means comprises switch means and said predetermined time period is a period of time sufficient to reduce to negligible levels the effects of the dielectric absorption of said capacitive means.

9. A method of calibrating and providing an output from a strain gauge after said strain gauge is fitted to an object to be measured comprising the steps of:

providing a constant current in said strain gauge;

detecting a difference between the voltage drop in said strain gauge due to said current and a reference voltage during a predetermined time period after said strain gauge is fitted to an object to be measured;

adjusting the magnitude of said constant current for reducing said voltage difference; and detecting the difference between the voltage drop in said strain gauge due to said current and said reference voltage after said adjusting of the magnitude of said current for providing an output of said voltage difference relative to said reference voltage.

10. A method according to claim 9 wherein said steps of detecting the difference between said voltage drop and said reference voltage and adjusting said current during said predetermined time period comprise the steps of:

charging a capacitor with a signal corresponding to said voltage difference for said predetermined time period; and coupling said capacitor to the source of said constant current.

11. A method according to claim 9 wherein said step of detecting the difference between said voltage drop and said reference voltage and said step of adjusting said current during said predetermined time period comprises the steps of:

providing a digital calibrating signal corresponding to the magnitude of the current from said current source by an amount corresponding to the magnitude of said stored digital calibrating signal.

12. A method according to claim 10 wherein said predetermined time period is a period of time sufficient to reduce to negligible levels the effects of the dielectric absorption of said capacitor.

13. A method according to claim 11 wherein said step of adjusting the magnitude of the current from said current source comprises the step of adjusting the magnitude of current from a digitally-controlled constant current source.

* * * * *